(12) United States Patent
Taniguchi

(10) Patent No.: US 8,830,308 B2
(45) Date of Patent: Sep. 9, 2014

(54) IMAGE MANAGEMENT APPARATUS, IMAGE MANAGEMENT METHOD AND COMPUTER-READABLE RECORDING MEDIUM ASSOCIATED WITH MEDICAL IMAGES

(71) Applicant: Olympus Medical Systems Corp., Tokyo (JP)

(72) Inventor: Katsuyoshi Taniguchi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/768,451

(22) Filed: Feb. 15, 2013

(65) Prior Publication Data
US 2013/0229503 A1    Sep. 5, 2013

Related U.S. Application Data

(63) Continuation of application No. PCT/JP2012/069199, filed on Jul. 27, 2012.

(30) Foreign Application Priority Data

Aug. 12, 2011  (JP) .................................. 2011-177135

(51) Int. Cl.
*A62B 1/04*     (2006.01)
(52) U.S. Cl.
USPC ........................................................... 348/65
(58) Field of Classification Search
USPC ........................................................... 348/65
See application file for complete search history.

(56) References Cited

U.S. PATENT DOCUMENTS

| | | | |
|---|---|---|---|
| 2008/0024599 A1* | 1/2008 | Hirakawa | 348/65 |
| 2008/0039692 A1* | 2/2008 | Hirakawa | 600/160 |
| 2009/0022400 A1 | 1/2009 | Matsuzaki | |

FOREIGN PATENT DOCUMENTS

| | | |
|---|---|---|
| JP | 5-205018 A | 8/1993 |
| JP | 2004-160103 A | 6/2004 |
| JP | 2005-149107 A | 6/2005 |
| JP | 2006-217046 A | 8/2006 |
| JP | 2007-75158 A | 3/2007 |
| JP | 2010-250188 A | 11/2010 |
| WO | 2009/013940 A1 | 1/2009 |
| WO | 2011/013475 A1 | 2/2011 |

OTHER PUBLICATIONS

International Search Report PCT/JP2012/069199 dated Oct. 2, 2012.

* cited by examiner

*Primary Examiner* — Chikaodili E Anyikire
*Assistant Examiner* — Leron Beck
(74) *Attorney, Agent, or Firm* — Scully, Scott, Murphy & Presser, P.C.

(57) ABSTRACT

An apparatus includes: a storage that stores operation information including information on an operation on a display screen of a medical image and reference feature data that are feature data of the medical image subjected to the operation; an acquiring unit that acquires image data corresponding to a series of medical images; a processor that calculates feature data of each medical image; a setter that compares the feature data calculated by the image processor with the stored reference feature data, and, when reference feature data having a correspondence to the feature data exist, sets, as information related to a display operation executed when the series of medical images are displayed on a screen, the information related to the operation associated with the reference feature data having the correspondence; and a controller that executes the set display operation when image data included in the series of medical images are played back.

18 Claims, 8 Drawing Sheets

FIG.7

D3: OPERATION INFORMATION
SELECTION SCREEN

PLEASE SELECT OPERATION INFORMATION

D31a      D32

| DOCTOR A | NUMBER OF OBSERVATIONS: ○○ <br> UPDATE DATE: ○○/○○/○○ |
| AVERAGE | NUMBER OF OBSERVATIONS: ○○ <br> UPDATE DATE: ○○/○○/○○ |

D31b

| DOCTOR B | NUMBER OF OBSERVATIONS: ○○ <br> UPDATE DATE: ○○/○○/○○ |

D31c

| DOCTOR C | NUMBER OF OBSERVATIONS: ○○ <br> UPDATE DATE: ○○/○○/○○ |

IMAGE MANAGEMENT APPARATUS, IMAGE MANAGEMENT METHOD AND COMPUTER-READABLE RECORDING MEDIUM ASSOCIATED WITH MEDICAL IMAGES

CROSS REFERENCES TO RELATED APPLICATIONS

This application is a continuation of PCT International Application Ser. No. PCT/JP2012/069199, which was filed on Jul. 27, 2012, designates the United States, and claims the benefit of priority from Japanese Patent Application No. 2011-177135 filed on Aug. 12, 2011, and the entire contents of the Japanese patent application and the PCT international application are incorporated herein by reference.

BACKGROUND OF THE INVENTION

1. Field of the Invention

The present invention relates to an image management apparatus, an image management method, and a computer-readable recording medium that display a medical image acquired by a capsule endoscope introduced into a subject.

2. Description of the Related Art

In examining a subject using a capsule endoscope that is introduced into the subject and captures an image inside a body of the subject, an operation of observing an image group acquired by the capsule endoscope as a pseudo-moving image or a list of still images and selecting those having abnormal findings are performed. This operation is referred to as observation. Normally, the image group captured by the capsule endoscope amounts to about 60,000 images (corresponding to about 8 hours), and thus it takes a very long time to observe all of the images and observing all of these takes a very long time and requires an ability to concentrate.

As functions of a screen (observation screen), which displays such an image group and is provided for observation by a health-care professional (for example, a medical doctor), for example, a function of continuously playing back the image group, a function of adjusting a playback speed, a pause function, a frame advance function, a list display function, and the like are available. Further, as functions of supporting the observation operation by the health-care professional, a function of automatically adjusting the playback speed, an automatic extraction function of automatically extracting images (for example, a red-colored image) with abnormal findings, and the like are known.

In addition, as a technique related to support for the observation, for example, Japanese Patent Application Laid-open No. 5-205018 discloses adding a priority order to images based on features detected from the images and displaying the images according to the priority order. Japanese Patent Application Laid-open No. 2004-160103 discloses reproducing a state similar to a previous display when a medical image data set of a locus similar to a previously displayed image data set is displayed on a medical image composite observation device. Japanese Patent Application Laid-open No. 2005-149107 discloses associating user information with a display database and storing information of a display format of a display screen for observation set by that user in the order of that display. PCT International Publication No. 2011/013475 discloses recording, with ordering, observation operation data input from an operation unit for an image being played back, and generating and displaying a series of images following the ordering using this observation operation data, such that a user is able to easily check a process of the observation performed in the past by the user or another observer.

SUMMARY OF THE INVENTION

An image management apparatus according to an aspect of the present invention has: an operation information storage unit that stores operation information including information related to a predetermined operation performed with respect to a screen on which a medical image is displayed and reference feature data that are feature data of the medical image subjected to the operation; an acquiring unit that acquires image data corresponding to a series of medical images; an image processing unit that calculates feature data of each medical image included in the series of medical images; a display operation information setting unit that compares the feature data calculated by the image processing unit with the reference feature data stored in the operation information storage unit, and, when the reference feature data having a correspondence to the feature data exist, sets, as information related to a display operation executed when the series of medical images are displayed on a screen, the information related to the predetermined operation associated with the reference feature data having the correspondence; and a control unit that executes the display operation set by the display operation information setting unit when image data included in the series of medical images are played back.

An image management method according to another aspect of the present invention includes: storing operation information including: information related to a predetermined operation performed with respect to a screen on which a medical image is displayed; and a reference feature data that is a feature data of the medical image subjected to the predetermined operation; acquiring image data corresponding to a series of medical images; executing image processing of calculating a feature data of each medical image included in the series of medical images; comparing the feature data calculated through the image processing with the reference feature data included in the stored operation information and, if the reference feature data having a correspondence with the feature data exist, setting the information related to the predetermined operation associated with the reference feature data having the correspondence as information related to a display operation executed when the series of medical images are displayed on a screen; and executing the set display operation when image data included in the series of medical images are played back.

A computer-readable recording medium according to yet another aspect of the present invention is a computer-readable recording medium storing an executable program that instructs a processor to execute: storing operation information including: information related to a predetermined operation performed with respect to a screen on which a medical image is displayed; and a reference feature data that is a feature data of the medical image subjected to the predetermined operation; acquiring image data corresponding to a series of medical images; executing image processing of calculating a feature data of each medical image included in the series of medical images; comparing the feature data calculated through the image processing with the reference feature data included in the stored operation information and, if the reference feature data having a correspondence with the feature data exist, setting the information related to the predetermined operation associated with the reference feature data having the correspondence as information related to a display operation executed when the series of medical images are displayed on a screen; and executing the set display operation when image data included in the series of medical images are played back.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a schematic diagram illustrating an example of the display of an operation information selection screen.

DETAILED DESCRIPTION OF THE PREFERRED EMBODIMENTS

Figure 1:
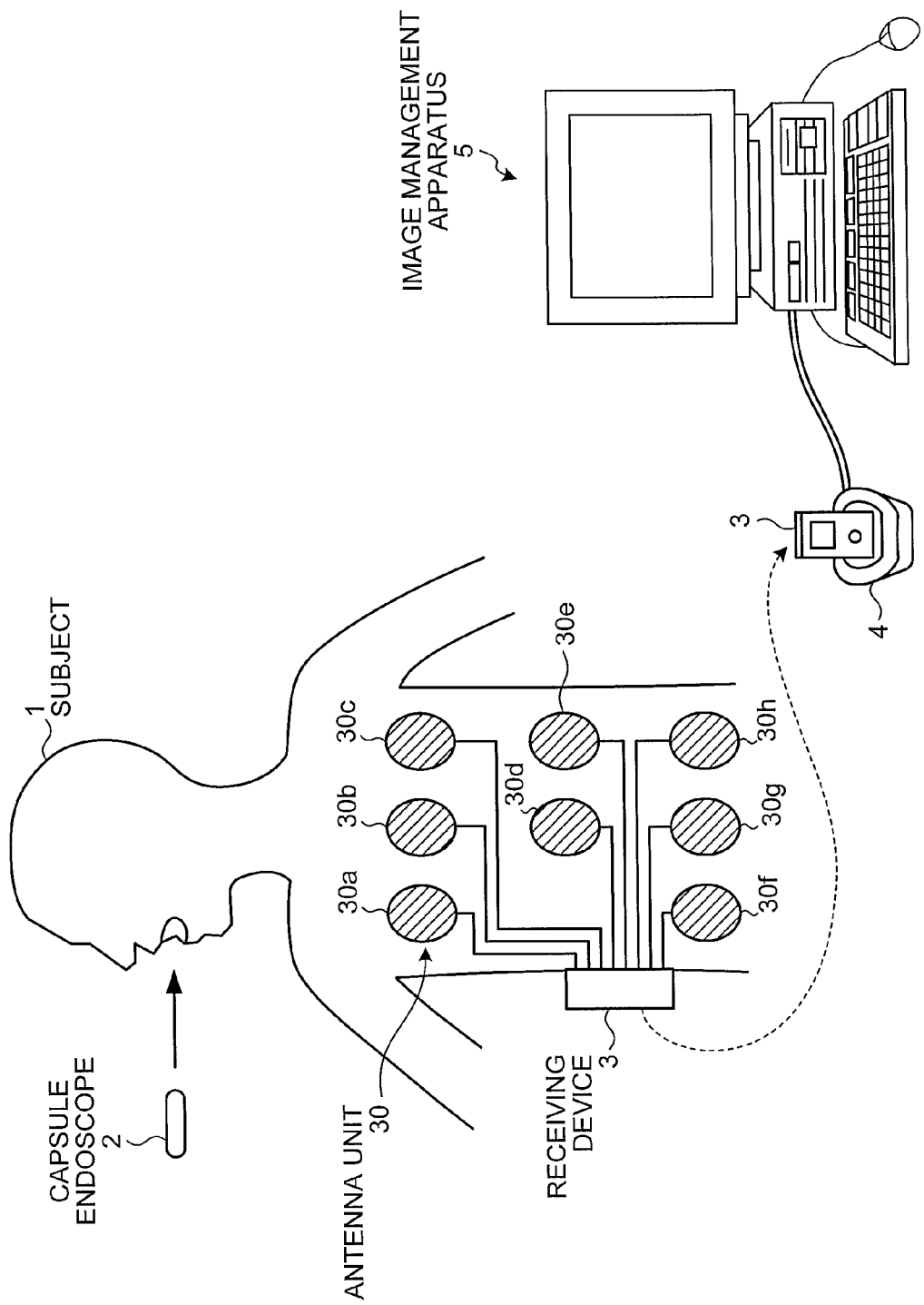
FIG. 1 is a schematic diagram illustrating an example of the schematic structure of a capsule endoscope system including an image management apparatus according to First Embodiment of the invention.

Hereinafter, an image management apparatus, an image management method, and a computer-readable recording medium according to embodiments of the invention will be described with reference to the accompanying drawings. In the following description, as an example, an image management apparatus is exemplified which manages a medical image (hereinafter, referred to as an in-vivo image) acquired by a capsule endoscope that is introduced into the body of a subject and captures the image of the inside of a digestive organ. However, the invention is not limited to the embodiment. In addition, in the following description, the drawings schematically illustrate the shape, size, and positional relation of components such that the content of the invention can be understood. Therefore, the invention is not limited only to the shape, size, and positional relation of the components illustrated in the drawings.

First Embodiment

FIG. 1 is a schematic diagram illustrating an example of the schematic structure of a capsule endoscope system including an image management apparatus according to First Embodiment of the invention. The capsule endoscope system illustrated in FIG. 1 includes a capsule endoscope 2 that is introduced into the body of a subject 1, captures an in-vivo image, and wirelessly transmits image data corresponding to the in-vivo image, a receiving device 3 that receives the image data wirelessly transmitted from the capsule endoscope 2, and an image management apparatus 5 that manages the in-vivo image based on the image data which is transmitted from the receiving device 3 through a cradle 4.

The capsule endoscope 2 includes an illumination element that illuminates the inside of the subject, a condenser lens that condenses light reflected from the inside of the subject, an imaging element, such as a CCD that converts the received light into an electric signal (image signal), an IC forming a signal processing unit that processes the image signal acquired by the imaging element, and various components such as a wireless transmission antenna. The capsule endoscope 2 is swallowed from the mouth of the subject 1 and sequentially captures the images of parts of the body (for example, the esophagus, the stomach, the small intestine, and the large intestine) at a predetermined time interval (for example, an interval of 0.5 seconds) while being moved in the digestive organs of the subject 1 by, for example, the peristaltic motion of the organs. Then, the capsule endoscope 2 performs predetermined signal processing on the image signal obtained by the imaging operation to generate image data and sequentially wirelessly transmits the image data and information related to the image data to the receiving device 3.

The receiving device 3 receives the image data and the related information which are wirelessly transmitted from the capsule endoscope 2 through an antenna unit 30 including a plurality of (eight in FIG. 1) receiving antennas $30a$ to $30h$. Each of the receiving antennas $30a$ to $30h$ is implemented by, for example, a loop antenna and is arranged at a predetermined position (for example, a position corresponding to each organ in the subject 1 which is a passage of the capsule endoscope 2) on the outer surface of the body of the subject 1.

The receiving device 3 is held by the subject 1 while the capsule endoscope 2 is capturing images (for example, while the capsule endoscope 2 is introduced from the mouth of the subject 1, passes through the digestive organs, and is excreted from the body). The receiving device 3 further adds, for example, related information, such as reception strength information or reception time information of each of the receiving antennas $30a$ to $30h$, to the image data received through the antenna unit 30, and stores the image data and the related information in memory provided therein. After the capture of the images by the capsule endoscope 2 ends, the receiving device 3 is detached from the subject 1 and is then set to the cradle 4 which is connected to, for example, a USB port of the image management apparatus 5. In this way, the receiving device 3 is connected to the image management apparatus 5, and the image data and the related information stored in the memory provided in the receiving device 3 are transmitted to the image management apparatus 5.

The transmission of, for example, the image data to the image management apparatus 5 is not limited to the method of transmitting the image data through the cradle 4. For example, when the image data stored in a server is processed, the image data may be acquired through a communicate device connected to the server. When image data stored in a portable recording medium, such as a CD-R or a DVD-R, is processed, for example, a reading device provided in the image management apparatus 5 may read the image data from the recording medium. Alternatively, a medical observation device may be connected to the image management apparatus 5 and image data may be directly acquired from the medical observation device.

The image management apparatus 5 is implemented by, for example, a workstation or a personal computer including a display means such as a monitor. The image management apparatus 5 displays some or all of the input in-vivo images as pseudo-moving images or still images on the screen using, for example, observation software, which will be described below. The user (observer) observes the in-vivo image displayed on the screen of the image management apparatus 5 and diagnoses, for example, the medical condition of the subject 1.

Figure 2:
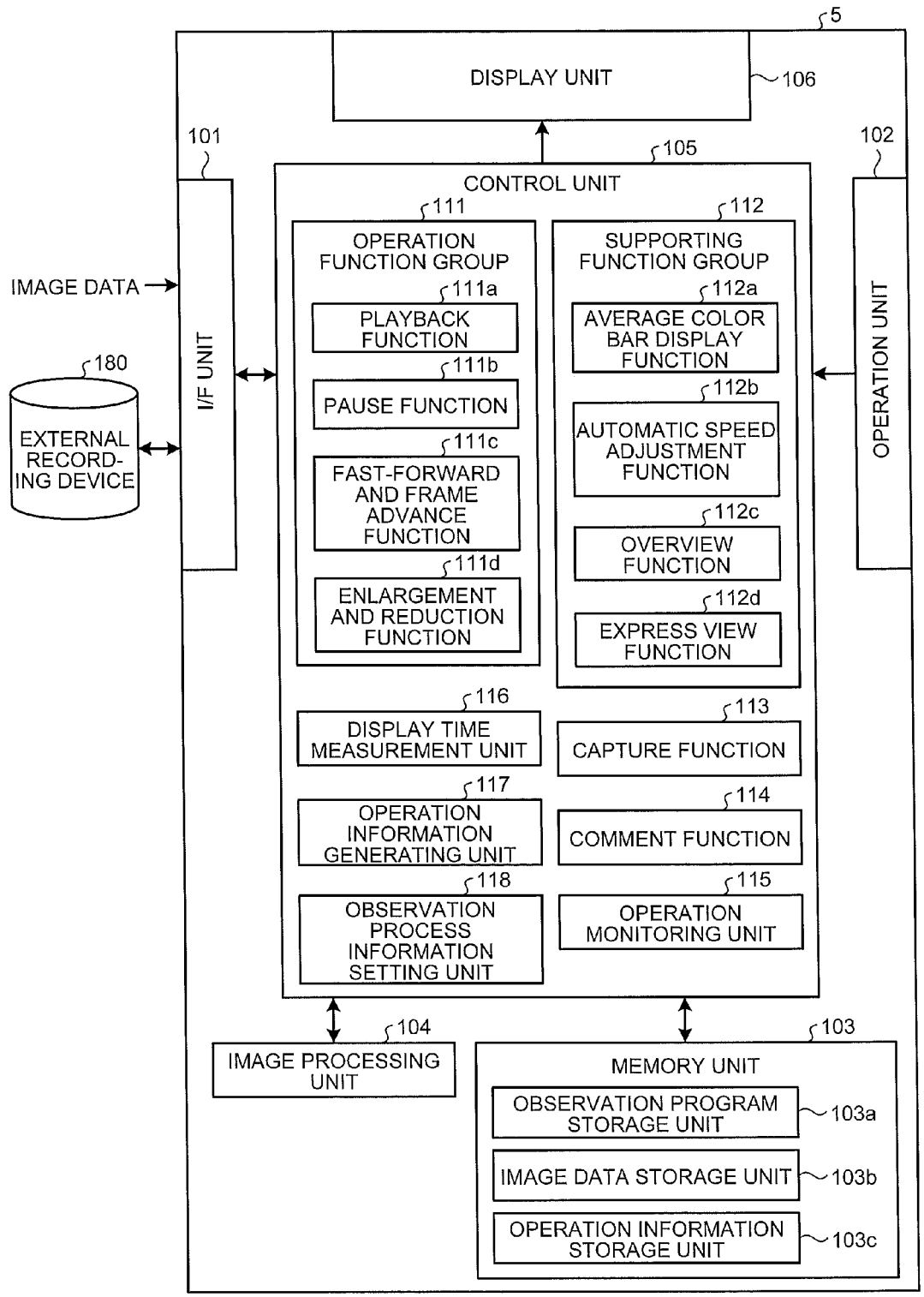
FIG. 2 is a block diagram illustrating the structure of the image management apparatus according to First Embodiment of the invention.

As illustrated in FIG. 2, the image management apparatus 5 includes an interface (I/F) unit 101 that receives input of image data corresponding to the in-vivo image, an operation unit 102 that is used by the user to input information about an observation operation or other operations, a memory unit 103 that stores the image data input from the interface unit 101, an image processing unit 104 that performs image processing for the image data input from the interface unit 101, a control unit 105 that provides the observation environment of the image data input from the interface unit 101 and controls the operation of each unit in the image management apparatus 5, and a display unit 106 that displays an observation GUI screen (hereinafter, referred to as an observation screen) including the in-vivo image or other screens under the control of the control unit 105. The image management apparatus 5 may further include an external recording device 180 that stores the image data of the input in-vivo image.

The interface unit 101 includes a connection port (for example, a USB port) to an external device (for example, a reading device which reads image data from a portable recording medium) and functions as an image acquiring unit that receives the input of signals indicating the image data which is input through the connection port and information related to the image data.

The operation unit 102 is implemented by, for example, an input device, such as a keyboard, a mouse, a touch panel, or various kinds of switches. The operation unit 102 receives the input of an operation signal corresponding to the operation of the user and inputs the operation signal to the control unit 105.

The memory unit 103 is an embedded storage device which is implemented by semiconductor memory, such as flash memory, RAM, or ROM, or a recording medium, such as an HDD, an MO, a CD-R, or a DVD-R, and a driving device for driving the recording medium. The memory unit 103 stores, for example, the image data of the in-vivo image, various kinds of programs executed by the control unit 105, and various kinds of setting information. Specifically, the memory unit 103 includes an observation program storage unit 103a that stores an observation program executed by the control unit 105, an image data storage unit 103b that stores image data and information related to the image data, and an operation information storage unit 103c that stores operation information used to set information about display when the in-vivo image is displayed on the observation screen.

The image processing unit 104 performs predetermined image processing for the image data input from the interface unit 101 to generate image data for display corresponding to each in-vivo image and calculates the feature data of each in-vivo image.

The control unit 105, by reading the observation program stored in the memory unit 103, executes: generating the observation screen including the in-vivo image; causing the display unit 106 to display the observation screen; and various functions in the observation screen according to the operation signals input from the operation unit 102 or according to information set by the observation process information setting unit 118 described later.

The functions on the observation screen include an operation function group 111 for, for example, playing back the in-vivo image, a supporting function group 112 for supporting the observation of the in-vivo image displayed on the display unit 106, a capture function 113 for capturing the displayed in-vivo image as an image of interest, and a comment function 114 for adding the command input by the user to the displayed in-vivo image. Although not illustrated in the drawings, a label function for adding the label selected by the user to the displayed in-vivo image may be provided. Examples of the label include labels for organs, such as the stomach, the small intestine, and the large intestine, and labels for lesions, such as hemorrhage, tumors, and ulcers.

The operation function group 111 includes, for example, a playback function 111a, a pause function 111b, a fast-forward and frame advance function 111c, and an enlargement and reduction function 111d. The playback function 111a is a function of continuously playing back a series of in-vivo images on the display unit 106 (a pseudo-moving image playback function). The pause function 111b is a function of stopping continuous playback and for continuously displaying the in-vivo image which is displayed at the time of stop. The fast-forward and frame advance function 111c is a function of increasing or decreasing the playback speed of a series of in-vivo images. The enlargement and reduction function 111d is a function of enlarging or reducing the in-vivo image to be displayed.

The supporting function group 112 includes, for example, an average color bar display function 112a, an automatic speed adjustment function 112b, an overview function 112c, and an express view function 112d. The average color bar display function 112a is a function that extracts color information of a series of in-vivo images in time series, generates a stripe image (average color bar) along a time axis from the extracted color information, and displays the generated average color bar as a GUI (Graphical User Interface) function component on the display unit 106. The automatic speed adjustment function 112b is a function that displays the in-vivo image as a pseudo-moving image while adjusting the display frame rate based on display frame rate information added to the image data corresponding to a series of in-vivo images. The overview function 112c is a function that reduces some images which are extracted from a series of in-vivo images under predetermined conditions and displays a list of the reduced images as a list of still images (displaying an overview screen). The express view function 112d is a decimated display function of displaying only some images which are extracted from a series of in-vivo images under predetermined conditions as pseudo-moving images (displaying an express view screen).

The control unit 105 includes an operation monitoring unit 115 that monitors various operations performed on the observation screen based on the operation signal input from the operation unit 102, a display time measuring unit 116 that measures the total display time of the in-vivo image displayed on the display unit 106, an operation information generating unit 117, and the observation process information setting unit 118. The operation information generating unit 117 generates operation information in which the content of an operation when any operation is performed on the observation screen and/or parameters of the operation, and the feature data of the in-vivo image to which the operation is applied are associated with each other. The observation process information setting unit 118 is a display operation information setting unit that sets information (hereinafter, referred to as observation process information) about a display operation performed when the in-vivo image is displayed on the observation screen based on the feature data of the in-vivo image and the operation information.

The observation process is a display operation which is performed on the observation screen when a series of in-vivo images is observed and includes, specifically, an operation of playing back the in-vivo image at a predetermined display frame rate or an operation of temporarily stopping the playback of the in-vivo image. In some cases, the display operation is performed by the manual operation of the user or it is performed by the automatic control of the control unit 105 based on predetermined information. The observation process information setting unit 118 sets information (specifically, for example, a display frame rate setting parameter or a parameter for extracting the image with a predetermined feature) which is used in the latter case.

Figure 3:
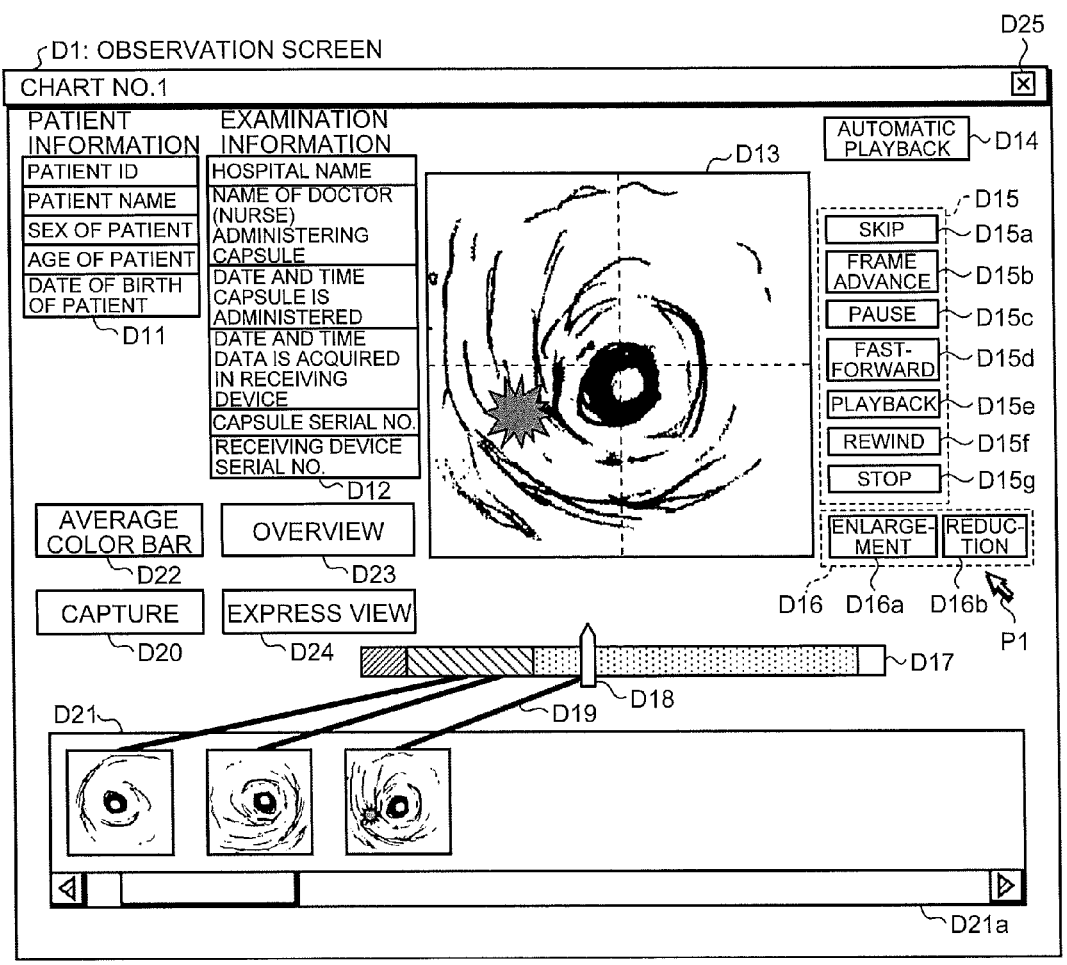
FIG. 3 is a schematic diagram illustrating an example of the display of an observation screen generated by the image management apparatus illustrated in FIG. 2.

Next, the observation screen displayed on the display unit 106 will be described in detail. FIG. 3 is a schematic diagram illustrating an example of the display of the observation screen.

As illustrated in FIG. 3, an observation screen D1 includes patient information D11 for identifying the subject 1 who is a patient, examination information D12 for identifying examination performed on the subject 1, a main display area D13 in which a series of in-vivo images is played back, an automatic playback setting button D14 for the user to input an instruction to cause the in-vivo image to be automatically played back in the main display area D13, a playback operation button group D15 for the user to control the playback of the in-vivo image in the main display area D13, a reduced scale operation button group D16 for the user to control the reduced scale of the in-vivo image in the main display area D13, an average color bar D17 which is generated from a series of in-vivo images, a capture button D20 for the user to input an instruction to capture the in-vivo image displayed in the main display area D13, a captured image display area D21 in which a list of the captured in-vivo images or the reduced images is displayed as a thumbnail, an average color bar button D22 for the user to input an instruction to cause the average color bar D17 to be displayed on the observation screen D1, an overview button D23 for the user to input an instruction to cause the display unit 106 to display the overview screen, and an express view button D24 for the user to input an instruction to cause the display unit 106 to display the express view screen.

The playback operation button group D15 is a group of buttons which are used by the user to input, to the operation function group 111, an instruction to control the playback of the in-vivo image in the main display area D13. The playback operation button group D15 includes, for example, a skip button D15*a*, a frame advance button D15*b*, a pause button D15*c*, a fast-forward button D15*d*, a playback button D15*e*, a rewind button D15*f*, and a stop button D15*g*.

The skip button D15*a* is a button for the user to input an instruction to return the in-vivo image to be played back in the main display area D13 to a first image in a series of in-vivo images. When the user clicks the skip button D15*a* by, for example, operating a pointer P1 on the observation screen D1 using the operation unit 102, the control unit 105 calls the playback function 111*a* and causes the playback function 111*a* to execute playback afresh from the first image in the series of in-vivo images on the main display area D13.

The frame advance button D15*b* and the fast-forward button D15*d* are used by the user to input instructions to decrease and increase the playback speed of a series of in-vivo images in the main display area D13, as compared to the normal playback speed. When the user operates, for example, the pointer P1 and clicks the frame advance button D15*b* or the fast-forward button D15*d*, the control unit 105 calls the fast-forward and frame advance function 111*c* and performs the fast-forward and frame advance function 111*c* to decrease or increase the playback speed of the in-vivo image in the main display area D13, as compared to the normal playback speed. When the frame advance button D15*b* or the fast-forward button D15*d* is clicked by the user, a predetermined speed may be decreased or increased according to the number of clicks. In this case, the playback speed of the in-vivo image in the main display area D13 can be changed in stages. Therefore, the user can effectively observe the in-vivo image.

The pause button D15*c* is used by the user to input an instruction to temporarily stop the continuous playback of a series of in-vivo images in the main display area D13. When the user operates, for example, the pointer P1 and clicks the pause button D15*c*, the control unit 105 calls the pause function 111*b* and performs the pause function 111*b* to stop the playback of the in-vivo images in the main display area D13 and to display the in-vivo image displayed in the main display area D13 immediately before the stop operation in the main display area D13. In order to resume the playback of the in-vivo image, the user operates the pointer P1 and clicks the pause button D15*c* again.

The playback button D15*e* is used by the user to input an instruction to start the playback of a series of in-vivo images in the main display area D13. When the user operates, for example, the pointer P1 and clicks the playback button D15*e*, the control unit 105 calls the playback function 111*a* and performs the playback function 111*a* to start the continuous playback of a series of in-vivo images in the main display area D13. For example, when reverse playback is performed, the control unit 105 changes playback by the playback function 111*a* from reverse playback to forward playback. The forward playback means playback in a chronological order.

The rewind button D15*f* is for the user to input an instruction to play back a series of in-vivo images in the main display area D13 in a sequence opposite to that of the chronological order, that is, an instruction for a reverse playback. When the user operates, for example, the pointer P1 and clicks the rewind button D15*f*, the control unit 105 calls the playback function 111*a* and performs the playback function 111*a* to start the continuous reverse playback of a series of in-vivo images in the main display area D13.

The stop button D15*g* is used by the user to input an instruction to stop the playback of the in-vivo image in the main display area D13. When the user operates the pointer P1 and clicks the stop button D15*g*, the control unit 105 calls, for example, the playback function 111*a* and performs the playback function 111*a* to stop the current playback/reverse playback operation.

The reduced scale operation button group D16 is a group of buttons which are used by the user to input an instruction to control the reduced scale of the in-vivo image in the main display area D13 to the operation function group 111. The reduced scale operation button group D16 includes an enlargement button D16*a* for inputting an instruction to narrow the display range of the in-vivo image and to display an enlarged in-vivo image in the main display area D13 and a reduction button D16*b* for inputting an instruction to widen the display range of the in-vivo image and to display a reduced in-vivo image in the main display area D13. When the user operates the pointer P1 and clicks the enlargement button D16*a* or the reduction button D16*b*, the control unit 105 calls the enlargement and reduction function 111*d* and performs the enlargement and reduction function 111*d* to display an enlarged or reduced in-vivo image.

As described above, the average color bar D17 converts the color information which is extracted along a time series from a series of in-vivo images into a bar-shaped image (average color bar) along the time axis. The user, by viewing the average color bar D17, is able to check how the average colors (in particular, tendency of red color) of the in-vivo images change through the series of in-vivo images along the time series. The average color bar D17 may be configured such that it is incorporated into the observation screen D1, for example, when the average color bar button D22 on the observation screen D1 is clicked. In this case, when the user operates, for example, the pointer P1 and clicks the average color bar button D22, the control unit 105 calls the average color bar display function 112a from the supporting function group 112 and generates the image of the average color bar D17 for a series of subject images. Then, the control unit 105 incorporates the generated average color bar D17 into a predetermined region of the observation screen D1. In this way, the observation screen D1 having the average color bar D17 incorporated thereinto is displayed on the display unit 106. In addition, a slider D18 indicating a position on the average color bar D17 corresponding to the in-vivo image which is displayed in the main display area D13 may be provided in the average color bar D17.

A list of the in-vivo images which are instructed to be captured by the user or the reduced images (hereinafter, referred to as thumbnail images or captured images) of the in-vivo images is displayed in the captured image display area D21 along the time series. A slider D21a used to slide the display range is provided in the captured image display area D21. The thumbnail image may be a reduced image or a decimated image of a target in-vivo image. In addition, a connection line D19 indicating the correspondence between the thumbnail image in the captured image display area D21 and the position on the average color bar D17 may be provided.

When the user uses, for example, the operation unit 102 to move the pointer P1 on the observation screen D1 and clicks the capture button D20, the control unit 105 calls the capture function 113. The capture function 113 specifies the in-vivo image displayed in the main display area D13 when the capture button D20 is clicked and adds a flag for identifying the capture image to image data corresponding to the in-vivo image. Alternatively, the capture function 113 may store the image data corresponding to the specified in-vivo image in a storage area which is ensured in, for example, a separate memory unit 103. In this way, the captured image is registered. In addition, the capture function 113 acquires or generates the in-vivo image which is registered as the captured image or the thumbnail image thereof and arranges and displays the in-vivo images in the captured image display area D21 along the time series.

When the user operates, for example, the pointer P1 and clicks the overview button D23, the control unit 105 calls the overview function 112c from the supporting function group 112. For example, the overview function 112c reads some in-vivo images from the image data storage unit 103b (or the external recording device 180) under predetermined conditions, generates an overview screen for displaying a list of the in-vivo images along the time series, and displays the overview screen on the display unit 106. The in-vivo image read by the overview function 112c may be, for example, an in-vivo image (for example, a captured image) having a predetermined identification flag added thereto or an in-vivo image with a predetermined feature data. The user can browse the overview screen to check or compare a plurality of in-vivo images at the same time.

When the user operates, for example, the pointer P1 and clicks the express view button D24, the control unit 105 calls the express view function 112d from the supporting function group 112. For example, the express view function 112d reads some in-vivo images from the image data storage unit 103b (or the external recording device 180), generates an express view screen for displaying the in-vivo images as moving images, and displays the express view screen on the display unit 106. The in-vivo image read by the express view function 112d may be, for example, an in-vivo image (for example, a captured image) having a predetermined identification flag added thereto or an in-vivo image with a predetermined feature data. The user can browse the express view screen from which the in-vivo image which is not required to be observed is decimated to continuously observe only the images which are required to be observed.

Figure 4:
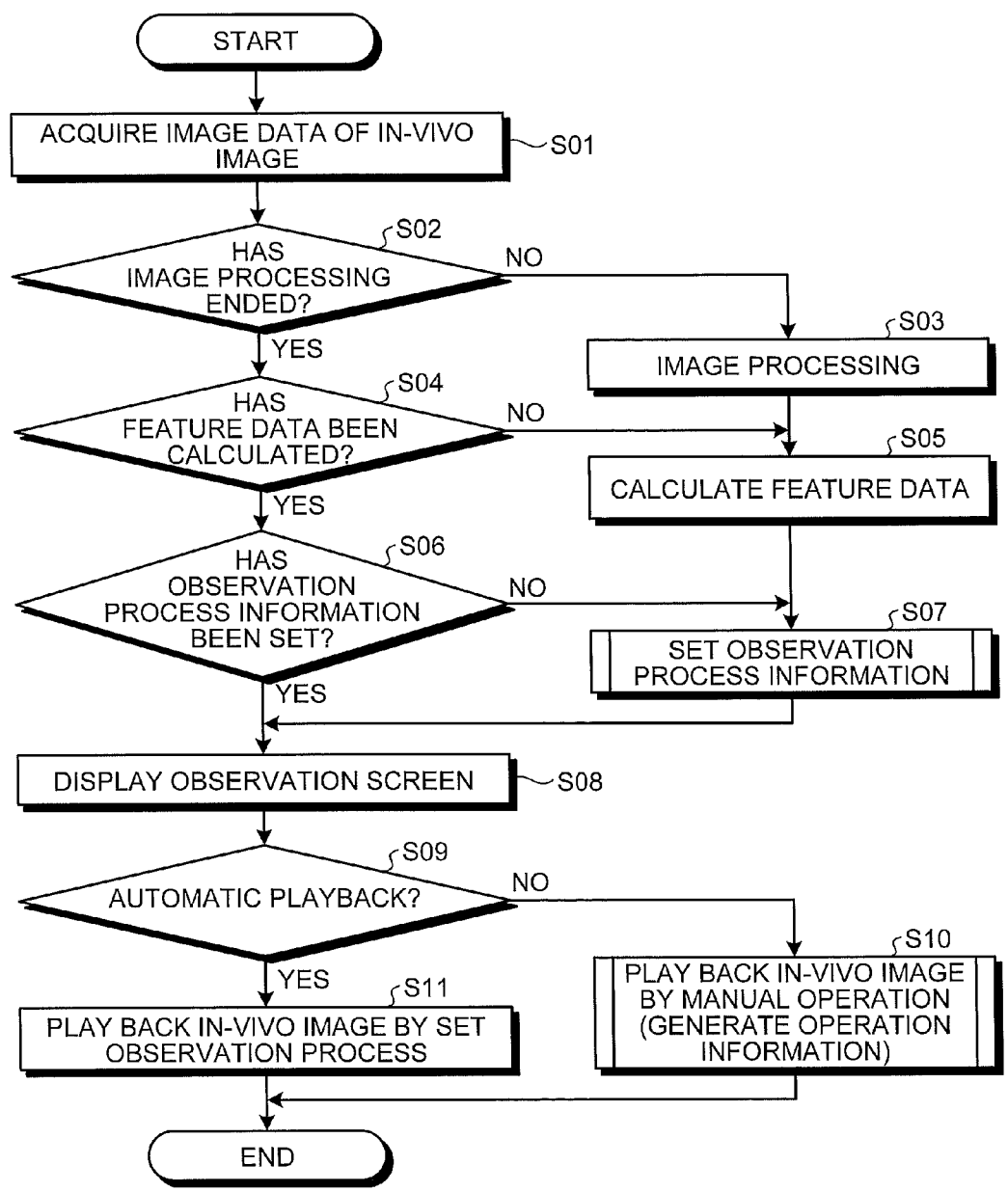
FIG. 4 is a flowchart illustrating the operation of the image management apparatus illustrated in FIG. 2.

Next, the operation of the image management apparatus 5 according to First Embodiment will be described. FIG. 4 is a flowchart illustrating an operation information generating process.

First, in Step S01, the image management apparatus 5 sequentially acquires image data corresponding to a series of in-vivo images captured by the capsule endoscope 2 and information related to the image data from the receiving device 3 through the cradle 4. The acquisition of the image data by the image management apparatus 5 is not limited to the method of acquiring the image data through the cradle 4. For example, when the image data stored in the server is processed, it may be acquired through a communicate device connected to the server. When image data stored in a portable recording medium, such as a CD-R or a DVD-R, is processed, for example, a reading device provided in the image management apparatus 5 or an external reading device may read the image data from the recording medium. Alternatively, a medical observation device may be connected to the image management apparatus 5 and image data may be directly acquired from the medical observation device.

Then, in Step S02, the control unit 105 determines whether the acquired image data has been subjected to predetermined image processing. When the image data has not been subjected to the image processing (No in Step S02), the image processing unit 104 sequentially performs image processing, such as white balance processing, demosaicing, color conversion, density conversion (for example, gamma conversion), smoothing (for example, noise removal), or sharpening (for example, edge emphasis), for the acquired image data to generate display image data corresponding to a series of in-vivo images, and stores the display image data in the image data storage unit 103b (Step S03).

On the other hand, when the acquired image data has been subjected to the predetermined image processing (Yes in Step S02), the control unit 105 stores the acquired image data in the image data storage unit 103b and determines whether the feature data of each in-vivo image has been calculated (Step S04). When the feature data has not been calculated (No in Step S04), the image processing unit 104 calculates one or plural kinds of feature data for each in-vivo image and stores the feature data in the image data storage unit 103b so as to be associated with the corresponding image data (Step S05). Specifically, as the feature data, for example, an average color (average values for respective components of RGB pixel values, average values of hue values, chroma, and lightness calculated from the RGB pixel values, or the like) of the in-vivo image, a variation in the average color from a previous image (an image which is captured immediately before in the time series), an average brightness of the in-vivo image, a variation in the average brightness from the previous image, a color (RGB values, a hue value, chroma, lightness, or the like) or brightness of one or a plurality of specific portion or portions (for example, a center of the in-vivo image, a few points that in a predetermined distance from the center, or the like) in the in-vivo image, a variation in the color or brightness in the specific portion or portions from the previous image, a concordance rate between a shape of the specific portion or portions and a specific pattern (for example, a pattern of a predetermined lesion), similarity to the previous image or a magnitude of a motion vector, a parameter indicating a locus (in-vitro, a mucous membrane region, or a non-mucous membrane region, or an organ type (stomach, small intestine, large intestine, or the like)) which is detected in the in-vivo image by known image processing, or a parameter indicating a specific pattern of a spatial frequency which is obtained by frequency analysis with respect to the in-vivo image, is calculated. For example, a characteristic pattern appears in the mucous membrane in a certain type of lesion, like celiac disease, for example, and thus when a spatial frequency of a predetermined band is extracted by frequency analysis, it is possible to observe a specific pattern. In addition, a weight may be given to each of the RGB components to calculate the feature data. For example, a large weight may be given to an R component and a G component which are likely to reflect the internal state of the body and a small weight may be given to the B component which is less likely to reflect the internal state of the body, thereby calculating the average color. In addition, a value obtained by weighted-summing a plurality of parameters indicating a variation in the similarity or the motion vector from the previous image may be acquired as the feature data.

The image processing unit 104 calculates the feature data of the image data which has been subjected to the image processing in Step S03 using the same method as described above.

Then, the process returns to the main routine.

When the feature data of the in-vivo image has been calculated (Yes in Step S04), the control unit 105 determines whether observation process information is set to a series of in-vivo images (Step S06). Specifically, the control unit 105 determines whether the parameters which are used in an operation of displaying the in-vivo image are stored so as to be associated with the image data corresponding to each in-vivo image. When the parameters are stored, the control unit 105 determines that the observation process information has been set. When the observation process information has not been set (No in Step S06), the observation process information setting unit 118 sets observation process information to a series of in-vivo images (Step S07).

On the other hand, when the observation process information has been set (Yes in Step S06), the control unit 105 sequentially reads image data from the image data storage unit 103b, generates, for example, the observation screen D1 illustrated in FIG. 3, and displays the observation screen D1 on the display unit 106 (Step S08).

Then, in Step S09, the control unit 105 determines whether the user uses, for example, the operation unit 102 to move the pointer P1 on the observation screen D1 and clicks the automatic playback setting button D14 to select the automatic playback mode. When the automatic playback mode is not selected (No in Step S09), the in-vivo image is played back by the manual observation process of the user (Step S10).

On the other hand, when the automatic playback mode is selected (Yes in Step S09), the control unit 105 automatically plays back the in-vivo image based on the set observation process information (Step S11). Alternatively, when the pointer P1 is operated on the observation screen D1 to click the overview button D23 or the express view button D24, the control unit 105 may extract the in-vivo image based on the parameters which are associated with each in-vivo image and generate an overview screen or an express view screen including the extracted in-vivo image.

Then, the process ends.

Playback of In-Vivo Image by Manual Observation Process (Generation of Operation Information)

Figure 5:
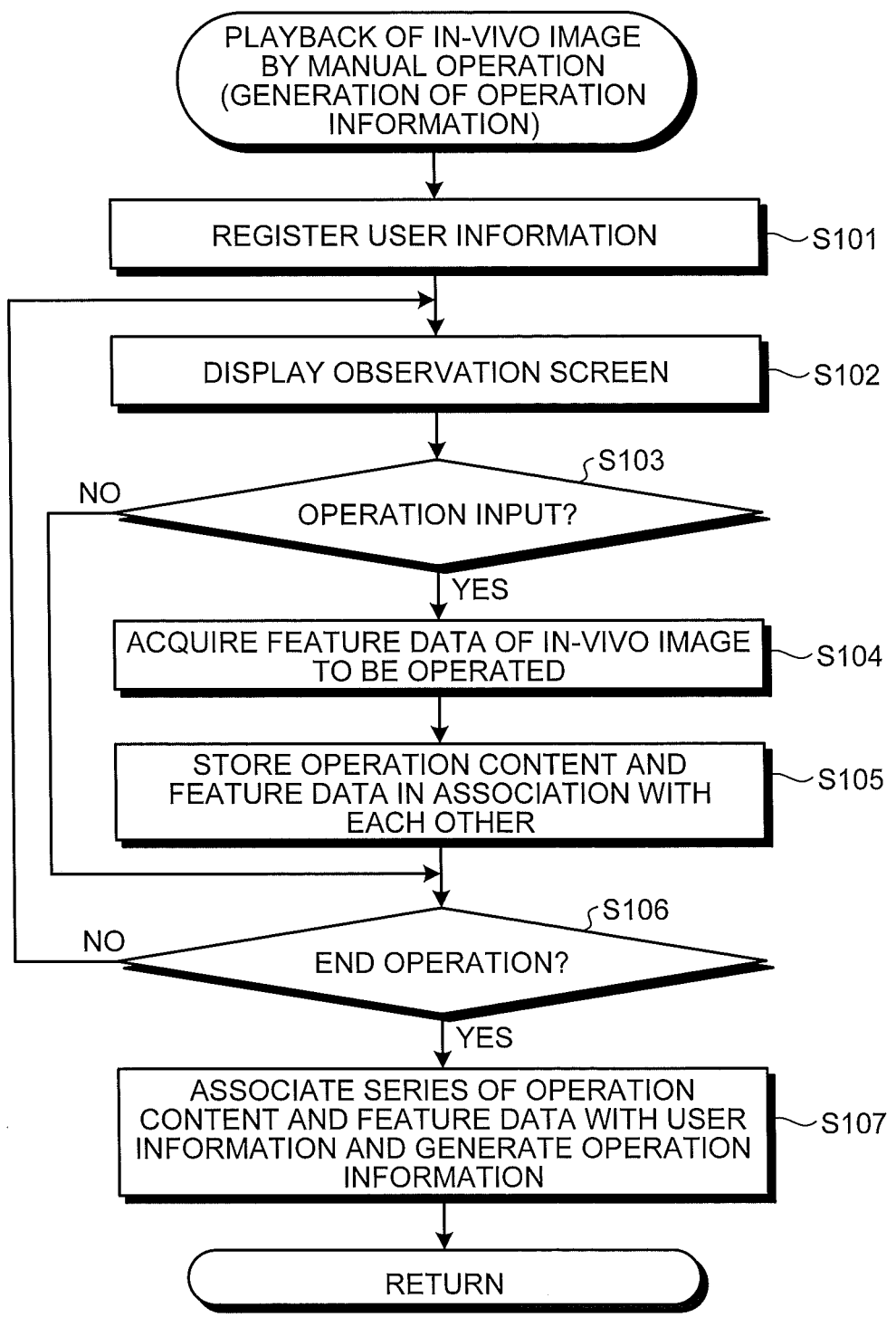
FIG. 5 is a flowchart illustrating an operation of playing back an in-vivo image (generating operation information) using a manual observation process.

Next, the playback of the in-vivo image by the manual observation process (Step S10) will be described. In this case, the control unit 105 also generates operation information at the same time. FIG. 5 is a flowchart illustrating the playback of the in-vivo image by the manual observation process (the generation of operation information).

First, in Step S101, the control unit 105 registers user information. As a method of registering the user information, for example, the following methods may be used: a method of displaying a predetermined user information registration screen on the display unit 106 of the image management apparatus 5 and inputting necessary information using the operation unit 102; and a method of reading bar codes on, for example, a name card using a bar code reader (not illustrated).

In Step S102, the control unit 105 generates, for example, the observation screen D1 illustrated in FIG. 3 based on the image data stored in the image data storage unit 103b and displays the observation screen D1 on the display unit 106.

In Step S103, the operation monitoring unit 115 determines whether the operation unit 102 receives an operation input to the displayed observation screen D1. Examples of the operation input to the observation screen include an operation for changing the display speed of the in-vivo image (a frame advance operation or a fast-forward operation), an operation for repeatedly displaying the in-vivo image, an operation for temporarily stopping playback, an operation for changing the playback direction (forward playback or reverse playback), an operation for enlarging or reducing the in-vivo image, an operation for changing image display parameters, such an operation for emphasizing a structure in the in-vivo image or an operation for changing a color or brightness, an operation for capturing the in-vivo image, an operation for adding a landmark to an in-vivo image indicating a predetermined position (for example, the boundary of an organ, such as the entrance of the small intestine), an operation for adding a comment or a label to the in-vivo image, an operation for attaching the captured in-vivo image to a report, a threshold value setting operation for displaying the overview screen, a threshold value setting operation for displaying the express view screen, and an operation for setting the number of in-vivo images displayed on the overview screen or the express view screen.

When an operation input to the observation screen D1 is received (Yes in Step S103), the operation information generating unit 117 acquires the feature data of the in-vivo image to be operated, from the image data storage unit 103b (Step S104). The acquired feature data may be one or plural kinds of predetermined feature data or one or plural kinds of feature data which are predetermined according to the content of the input operation. When the input operation is received, the operation information generating unit 117 may direct the image processing unit 104 to calculate the feature data and acquire the feature data.

In Step S103, when an operation for temporarily stopping the playback of the in-vivo image or an operation for temporarily stopping playback and performing reverse playback is received, the feature data of the in-vivo image corresponding to the time when the pause operation is received, or the amount of the in-vivo image that is a predetermined number of in-vivo images before the time when the pause operation is received may be acquired. This is because there is a time lag from the time when the user recognizes the necessity of checking the in-vivo image to the time when the pause operation is actually performed. In addition, a plurality of kinds of feature data may be extracted from one in-vivo image and the content of the operation may be associated with each of the extracted plurality of kinds of feature data.

When the feature data of the in-vivo image is acquired backward from the reception of the pause operation, the time or the number of in-vivo images which turns back from the reception of the pause operation may be set by a method corresponding to, for example, the playback mode. For example, when the time lag from the recognition of the in-vivo image to be checked to the reception of the pause operation is 0.5 seconds and the playback frame rate is 40 frames per second, the feature data of the in-vivo image that is 20 in-vivo images before the reception time is acquired. When the playback frame rate is 10 frames per second, the feature data of the in-vivo image that is five images before the reception time is acquired.

In Step S105, the operation information generating unit 117 stores the content of the operation received in Step S103 and the feature data acquired in Step S104 in the operation information storage unit 103c so as to be associated with each other. In this case, when the content of the operation indicates a reduction in the playback speed of the in-vivo image, the playback speed may also be stored. When the content of the operation indicates the repeated display of the in-vivo image, the number of display operations may also be stored. When the content of the operation indicates a pause, the time for which playback pauses (that is, the display time of the in-vivo image) may also be stored. When the content of the operation indicates the enlargement of the in-vivo image, an enlargement ratio (the number of times the enlargement button D16a is clicked) may also be stored.

On the other hand, when the input of the operation corresponding to the observation screen D1 is not received in Step S103 (No in Step S103), the process proceeds to Step S106.

In Step S106, the control unit 105 determines whether the operation unit 102 receives an end operation input to the displayed observation screen. The end operation corresponds to, for example, an operation of using a mouse to move the pointer P1 on the observation screen D1 and clicking a "close" button D25 or a predetermined keyboard operation. When the end operation is not received (No in Step S106), the process returns to Step S102.

On the other hand, when the end operation is received (Yes in Step S106), the operation information generating unit 117 generates a set of operation information in which the content of the operation stored in the operation information storage unit 103c by a series of observation operations and the feature data associated with the content are associated with the user information (Step S107). In this case, the operation information generating unit 117 may associate the operation information with related information such as a date. In addition, when a plurality of feature data are associated with the content of a common operation included in a series of operations, the operation information generating unit 117 may aggregate the feature data, calculate the average value of various kinds of feature data, and associate the average value with the content of the operation.

This process is repeatedly performed a plurality of times and a plurality of sets of operation information are stored in the operation information storage unit 103c. The operation information generating unit 117 may record the generated operation information on the external recording device 180 or an external recording device which is connected thereto through a communicate device.

Modification 1 of Generation of Operation Information

When the previously generated operation information is stored in the operation information storage unit 103c, the operation information generating unit 117 may calculate the average value or the weighted average value of a plurality of feature data which are associated with the content of a common operation between the currently generated operation information and the previously generated operation information to generate new operation information. In this way, it is possible to obtain operation information in which the experience of the observation operation performed in the image management apparatus 5 is accumulated. In this case, the operation information generating unit 117 may store operation information which is individually generated and operation information about the average of the individually generated operation information in the individual operation information storage unit 103c.

Modification 2 of Generation of Operation Information

When a plurality of sets of operation information associated with the user information of one user are stored in the operation information storage unit 103c, the operation information generating unit 117 may calculate the average value or the weighted average value of a plurality of feature data which are associated with the content of a common operation included in the plurality of sets of operation information to generate new operation information. In this way, it is possible to obtain operation information in which the experience of each user is accumulated.

Setting of Observation Process Information

Figure 6:
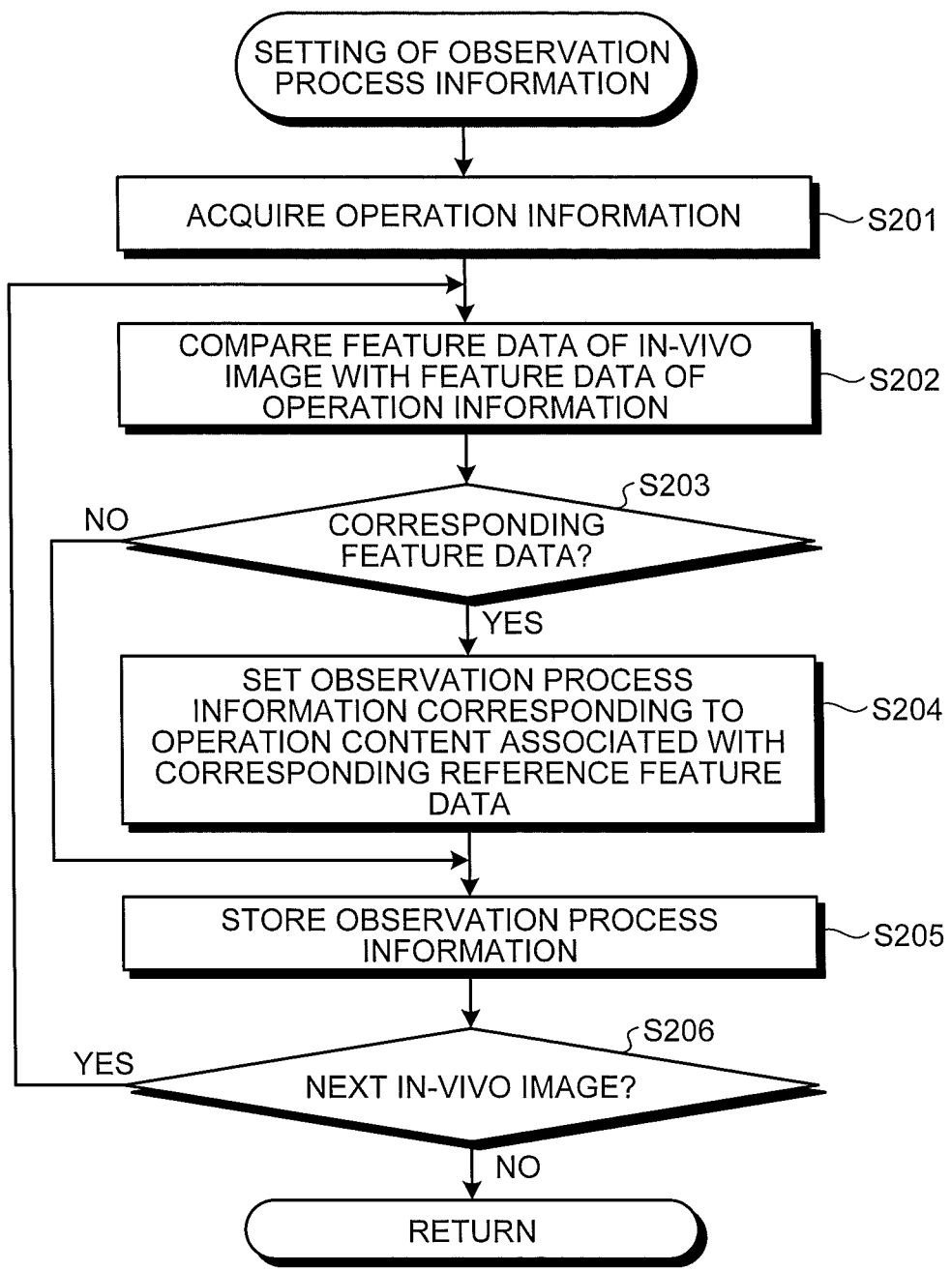
FIG. 6 is a flowchart illustrating an observation process information setting operation.

Next, the process of setting the observation process information (Step S07) will be described. FIG. 6 is a flowchart illustrating the process of setting the observation process information.

First, in Step S201, the observation process information setting unit 118 acquires the operation information stored in the operation information storage unit 103c.

In this case, when a plurality of sets of operation information are stored in the operation information storage unit 103c, the control unit 105 may display a screen for allowing the user to select the operation information on the display unit 106 such that the user selects desired operation information. FIG. 7 is a schematic diagram illustrating an example of the display of an operation information selection screen. An operation information selection screen D3 illustrated in FIG. 7 includes icons D31a to D31c and an icon D32 for allowing the user to distinguish and select each set of operation information stored in the operation information storage unit 103c. Among them, the names of the observers (doctor names) who perform the observation operation, which is an operation information generation source, are displayed in the icons D31a to D31c. In addition, "average" displayed in the icon D32 indicates operation information obtained by averaging the operation information based on the observation operation which has been previously performed in the image management apparatus 5. In addition, as reference information when the user selects operation information, the number of observations performed by each observer and the latest observation date (update date) are displayed in the vicinity of each of the icons D31a to D31c and the icon D32.

Alternatively, the observation process information setting unit 118 may acquire operation information from an external apparatus, such as a server, through a communication device.

In Step S202, the observation process information setting unit 118 compares the feature data (hereinafter, referred to as a subject feature data) of the in-vivo image with the feature data (hereinafter, referred to as a reference feature data) associated with the content of each operation in the operation information. Specifically, the observation process information setting unit 118 determines the correspondence that the subject feature data is equal to or more than the reference feature data or the subject feature data is within a predetermined range of the reference feature data. The kind (for example, an average color and brightness) of object and reference feature data to be compared may be appropriately set. In addition, one or plural kinds of feature data may be compared with each other. A method of comparing the subject feature data with the reference feature data may be determined according to the kind of feature data or the content of the operation associated with the reference feature data. For example, when the feature data is the average value of the R component, a variation in the average color or brightness, the concordance rate between the shape of a portion of the image with a specific pattern, and the magnitude of a motion parameter and the subject feature data is equal to or more than the reference feature data, it is determined that there is a correspondence between the subject feature data and the reference feature data. Alternatively, when the subject feature data is included in a predetermined range before and after the reference feature data, it may be determined that there is a correspondence between the subject feature data and the reference feature data.

When a reference feature data having a correspondence with the subject feature data (Yes in Step S203) is present, the observation process information setting unit 118 sets the observation process information corresponding to the content of the operation which is associated with the corresponding reference feature data to the in-vivo image with the subject feature data (Step S204). In a case in which a plurality of kinds of feature data are compared in Step S202, when there is a correspondence with at least one kind of feature data, the observation process information may be set. When there is a correspondence with all of the feature data, the observation process information may be set.

For example, a case in which the observation process information is a parameter (coefficient) $\alpha$ for determining the display frame rate when the playback speed of the in-vivo image is automatically adjusted will be described. In general, the display frame rate is set to about 16 frames per second and the parameter $\alpha$ is set to 1 which is a default value. In Step S204, the value of parameter $\alpha$ is changed in a predetermined range (for example, $0.3 \leq \alpha < 1$) under predetermined conditions. In this case, not only for the in-vivo image having the subject feature data but also for an in-vivo image in a predetermined range around that in-vivo image, the parameter $\alpha$ may be changed to the same extent. Alternatively, the parameter $\alpha$ of the in-vivo image having the subject feature data may be set to the minimum value $\alpha_0$ and the parameter $\alpha$ of the in-vivo image in the predetermined range therearound may be varied slopingly between $\alpha_0$ and 1.

The observation process information setting unit 118 may set the value of the parameter $\alpha$ according to the following priority order to speed adjustment. In the following description, priority becomes higher in the order from (1) to (8), and the higher the priority is, the smaller the value of parameter $\alpha$ is set. That is, the higher the priority is, the slower the playback speed is made (that is, the longer the display time per image is made) so that the user is able to take time to observe the in-vivo image.

(1) An in-vivo image with the subject feature data corresponding to the reference feature data associated with an operation of slowing displaying the in-vivo image (in this case, the slower the corresponding playback speed is, the higher the priority may be made);

(2) An in-vivo image with the subject feature data corresponding to the reference feature data associated with an operation of repeatedly displaying the in-vivo image (in this case, the greater the number of times the corresponding display has been made, the higher the priority may be made);

(3) An in-vivo image with the subject feature data corresponding to the reference feature data associated with the pause operation;

(4) An in-vivo image with the subject feature data corresponding to the reference feature data associated with an operation of temporarily stopping playback and reversely playing back the in-vivo image;

(5) An in-vivo image with the subject feature data corresponding to the reference feature data associated with an operation of enlarging the in-vivo image (in this case, the greater the corresponding enlargement ratio is, the higher the priority may be made);

(6) An in-vivo image with the subject feature data corresponding to the reference feature data associated with an operation of capturing the in-vivo image;

(7) An in-vivo image with the subject feature data corresponding to the reference feature data associated with an operation of adding a comment or a label to the in-vivo image; and (8) An in-vivo image with the subject feature data corresponding to the reference feature data associated with an operation of adding the captured in-vivo image to a report.

The user may set the priority order or the value of the parameter $\alpha$ in advance.

In Step S205, the control unit 105 stores the observation process information set by the observation process information setting unit 118 in the image data storage unit 103*b* so as to be associated with the image data of the corresponding in-vivo image.

When there is no reference feature data corresponding to the subject feature data in Step S203 (No in Step S203), the process proceeds to Step S205.

In Step S206, it is determined whether there is the next in-vivo image subjected to image processing and a feature data calculating process (Step S203). When there is the next in-vivo image (Yes in Step S206), the process returns to Step S202. On the other hand, when there is no next in-vivo image (No in Step S206), the process returns to the main routine.

The control unit 105 may record image data corresponding to a series of in-vivo images and observation process information associated with the image data to the external recording device 180 or an external recording device connected thereto through, for example, a communication device.

Modification 1 of Setting of Observation Process Information

In Step S204, various kinds of observation process information may be set, in addition to the parameter $\alpha$ of the display frame rate.

For example, an image extraction threshold value (image extraction parameter) for displaying the express view screen or the overview screen may be set as the observation process information. In this case, the value of the image extraction parameter may be changed depending on the same priority as the speed adjustment priority. Specifically, a weight is given to the image extraction parameter such that the in-vivo images are extracted in descending order of priority (that is, in the order of (8) to (1)).

Modification 2 of Setting of Observation Process Information

In Step S204, a landmark (for example, a specific part, such as the entrance of the small intestine, or the kind of organ) may be automatically added to the in-vivo image to be observed. In this case, a variation in the average color of the in-vivo image to which the landmark is added by a manual operation and the in-vivo images before and after the in-vivo image is used as the reference feature data corresponding to the landmark addition operation. The in-vivo image with the subject feature data corresponding to the reference feature data is set as a landmark estimated image.

In this case, on the observation screen D1, an estimated landmark (for example, a landmark represented by a dashed line) may be automatically displayed at a position corresponding to the landmark estimated image on the average color bar D17. In this way, the user can determine the position of the landmark to be added while referring to the displayed estimated landmark.

Alternatively, a flag indicating that playback automatically starts from an image may be added to the in-vivo image that is several images before the landmark estimated image such that playback starts from the in-vivo image that is several images before the landmark estimated image on the observation screen D1. In addition, the operation process information may be set such that the playback of the in-vivo image is temporarily stopped in the landmark estimated image.

Modification 3 of Setting of Observation Process Information

In Step S204, the interval at which the images are decimated when the express view screen is displayed may be set according to the kind of organ. In this case, a parameter indicating the kind of organ is used as the reference feature data. Specifically, for example, the observation process information setting unit 118 sets a threshold value $C_{SI}$ of the feature data of image extraction to the in-vivo image corresponding to the reference feature data indicating the small intestine and sets a threshold value $C_{LI}$ ($\neq C_{SI}$) of the feature data of image extraction to the in-vivo image corresponding to the reference feature data indicating the large intestine. In this case, only the in-vivo image with a feature data equal to or more than the threshold value $C_{SI}$ is extracted in the range of the in-vivo image corresponding to the small intestine and only the in-vivo image with a feature data equal to or more than the threshold value $C_{LI}$ is extracted in the range of the in-vivo image corresponding to the large intestine. In this way, the express view screen is generated.

Modification 4 of Setting of Observation Process Information

In Step S204, the playback speed of the in-vivo image with the subject feature data corresponding to the reference feature data which is associated with a fast-forward display operation may increase or the in-vivo image may not be displayed. In this case, the observation process information setting unit 118 sets the parameter α of the display frame rate of the in-vivo image to a large value (α>1), or sets the value of the playback image extraction parameter to a small value. In this way, it is possible to reduce the display time of the in-vivo image which does not need to be observed and improve the observation efficiency of the user.

As described above, according to First Embodiment, the observation process is set based on the operation information generated by collecting the operation performed by the user on the observation screen, not an image extraction algorithm which is individually developed based on the limited number of lesion images. Therefore, it is possible to display the in-vivo image in which the observation know-how of the user is reflected.

According to First Embodiment, it is possible to play back the in-vivo image using the observation process in which the experience of the user is accumulated. Therefore, it is possible to easily find abnormalities which are less likely to be found by an image extraction algorithm based on uniform determination.

According to First Embodiment, the manual observation operation is repeatedly performed to store the operation information in which the experience of the user is reflected. Therefore, it is possible to reinforce the observation process capable of reducing the possibility that abnormalities will not be found.

According to First Embodiment, it is possible to play back the in-vivo image using the observation process in which the experience of the user is accumulated. Therefore, a person who is not skilled in observation can learn the observation technique of a skilled person to acquire observation know-how.

According to First Embodiment, it is possible to play back the in-vivo image which is determined not to be observed based on the accumulated experience of the user at a high speed, or it is possible to omit the playback of the in-vivo image. Therefore, it is possible to improve observation efficiency and reduce the total observation time.

Modification 1 of First Embodiment

In First Embodiment, the content of the operation input to the observation screen and the feature data are associated with each other to generate the operation information. However, the parameter extracted from the content of the operation, not the content of the operation, may be associated with the feature data to generate the operation information. Specifically, the parameter of the display frame rate or a parameter, such as the image extraction threshold value, may be extracted from the content of the operation performed by the user and the extracted parameter may be associated with the feature data of an in-vivo image to be operated. In this case, the observation process information setting unit 118 may directly associate the parameter corresponding to the reference feature data which corresponds to the subject feature data with the image data to which the observation process information will be set. Therefore, it is possible to reduce the time request to set the observation process.

Modification 2 of First Embodiment

In First Embodiment, when the feature data of the in-vivo image is calculated, the observation process information is set. However, the observation process information may be reset (updated) as needed. For example, the observation process information may be set whenever the image data stored in the image data storage unit 103b is read. Alternatively, when the user inputs an instruction to set the observation process information, the observation process information may be set. In this case, the operation information stored in the image management apparatus 5 is updated or added whenever a manual observation operation is performed in the image management apparatus 5. Therefore, since the observation process information is reset, it is possible to play back and display the in-vivo image using the observation process in which a lot of user experience is reflected.

Second Embodiment

Next, Second Embodiment of the invention will be described.

Figure 8:
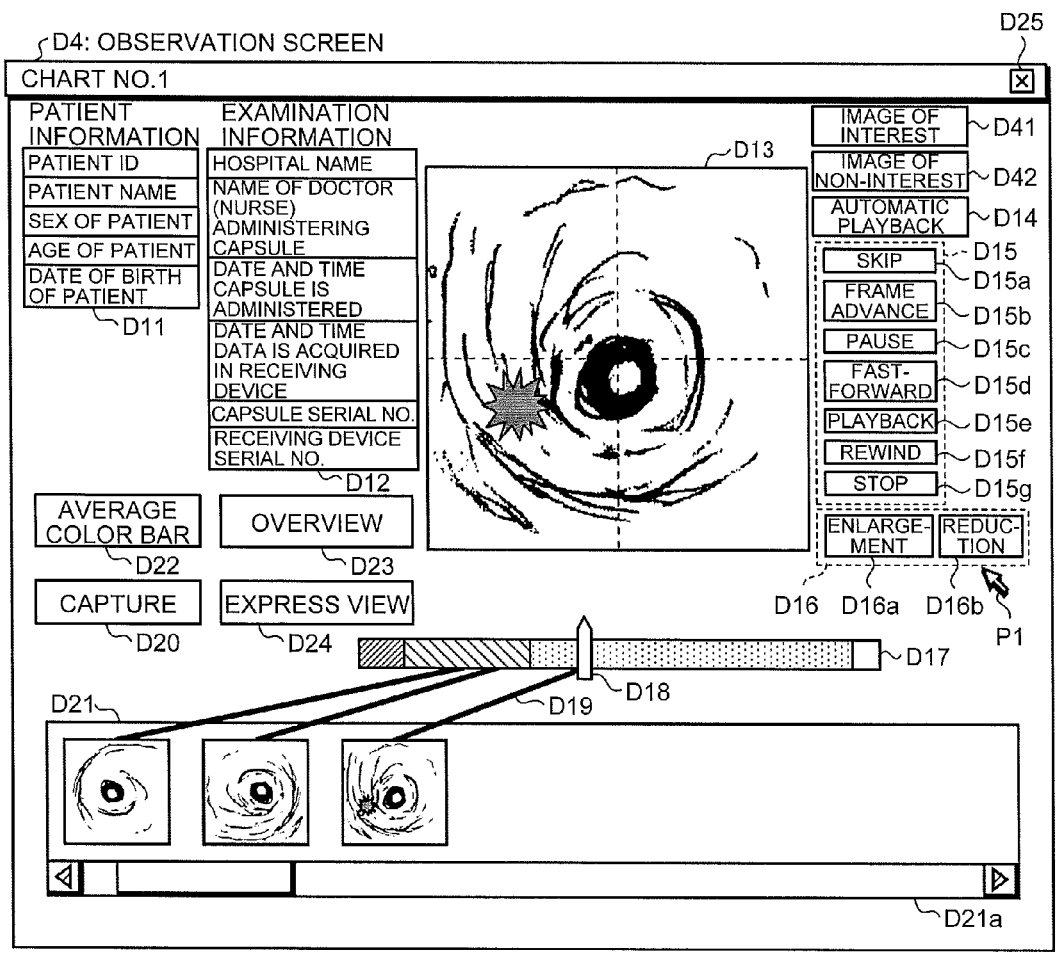
FIG. 8 is a schematic diagram illustrating an example of the display of an observation screen generated by an image management apparatus according to Second Embodiment of the invention.

FIG. 8 is a schematic diagram illustrating an example of the display of an observation screen in an image management apparatus according to Second Embodiment. The image management apparatus according to Second Embodiment has the same structure as that illustrated in FIG. 1.

An observation screen D4 illustrated in FIG. 8 is different from the observation screen D1 illustrated in FIG. 3 in that it further includes an image-of-interest button D41 and an image-of-non-interest button D42. The image-of-interest button D41 is used by the user to input an instruction to designate an in-vivo image displayed in a main display area D13 as an image of interest. The image-of-non-interest button D42 is used by the user to input an instruction to designate the in-vivo image displayed in the main display area D13 as an image of non-interest.

When the pointer P1 is operated on the observation screen D4 to select the image-of-interest button D41, the control unit 105 acquires the feature data of the in-vivo image displayed in the main display area D13, adds a flag (image-of-interest flag) indicating an image of interest, and stores the feature data as a reference feature data in the operation information storage unit 103c. When the pointer P1 is operated on the observation screen D4 to select the image-of-non-interest button D42, the control unit 105 acquires the feature data of the in-vivo image displayed in the main display area D13, adds a flag (image-of-non-interest flag) indicating an image of non-interest, and stores the feature data as the reference feature data in the operation information storage unit 103c. The kind of the acquired feature data of the in-vivo image is the same as that in First Embodiment.

When an in-vivo image observation process is set, the observation process information setting unit 118 compares the feature data (subject feature data) of the in-vivo image to be observed with a series of reference feature data. In this case, when the subject feature data corresponds to the reference feature data having the image-of-interest flag added thereto, the observation process information setting unit 118 sets, for example, an observation process of increasing the playback time (that is, an observation process of reducing the playback speed) to the in-vivo image with the subject feature data. As speed adjustment priority, the priority of an operation of adding the image-of-interest flag is higher than the priority of the operation of adding the captured in-vivo image to the report which is described in (8) of First Embodiment.

When the subject feature data corresponds to the reference feature data having the image-of-non-interest flag added thereto, the observation process information setting unit 118 sets, for example, an observation process of reducing the playback time (that is, an observation process of increasing the playback speed) to the in-vivo image with the subject feature data.

According to Second Embodiment, the user can intentionally set a specific feature of an in-vivo image of interest as the reference feature data, separately from an image observation operation. Therefore, it is possible to set the observation process according to preference of the user. In addition, the process of designating the image of interest and the image of non-interest can be repeatedly performed to reinforce the observation process capable of reducing the possibility that, for example, a lesion will not be found.

Modification of Second Embodiment

The reference feature data having the image-of-interest flag and the image-of-non-interest flag added thereto are shared with the operation information which is accumulated by a display operation (for example, an operation of repeatedly displaying the in-vivo image) on the observation screen. In this case, it is possible to give a weight to the observation process information or designate the application balance of the observation process information. For example, when the subject feature data corresponds to the reference feature data having the image-of-interest flag added thereto, a weight may be given to the observation process information based on the operation information which is set to the in-vivo image with the subject feature data. When the subject feature data corresponds to the reference feature data having the image-of-non-interest flag added thereto, the weight given to the observation process information based on the operation information which is set to the in-vivo image with the subject feature data may be reduced.

For example, when the range of the parameter of the playback frame rate which can be set by the observation process based on general operation information is from 0.3 to 1.0 (that is, deceleration is in the range of 70% to 0%), weighting can be performed based on the reference feature data having the image-of-interest flag added thereto to further increase the deceleration. For example, in the above-mentioned case, a weight coefficient of 1.3 can be given to a deceleration of 70% to increase the deceleration up to about 90% (that is, to reduce about a maximum of 10 percent of the general display speed).

Third Embodiment

Next, Third Embodiment of the invention will be described.

In First and Second Embodiments, the operation information is accumulated based on the operation performed for the observation screen displayed on the image management apparatus 5 (see FIG. 1) and the observation process information for performing various functions on the observation screen displayed on the image management apparatus 5 is set to the in-vivo image to be observed, using the operation information. However, the operation information accumulated in the image management apparatus 5 may be used to set observation process information in another image management apparatus.

In this case, the operation information stored in the operation information storage unit 103c is exported to the external recording device 180 through the I/F unit 101. Then, another image management apparatus in which the observation program according to First or Second Embodiment is installed may be connected to the external recording device 180, the operation information may be imported, and another image management apparatus may set the observation process information to a series of in-vivo images to be observed, based on the operation information. A method of setting the observation process information is the same as that in First Embodiment.

According to Third Embodiment, the operation information accumulated in the image management apparatus 5 can be shared by another image management apparatus to perform the observation process in which the experience of the user is accumulated in another image management apparatus. Therefore, the observation technique of the doctor who is skilled in observation can be used in other rooms or facilities.

A portable storage medium and a reading device for the portable storage medium may be used as the external recording device 180. In this case, a reading device connected to another image management apparatus may read the operation information stored in the portable storage medium. Alternatively, the operation information may be exported and imported between the image management apparatus 5 and another image management apparatus through a wired or wireless network. In addition, the operation information generated in another image management apparatus may be imported to the image management apparatus 5 to set the observation process information.

According to the above-described First to Third Embodiments of the invention and the modifications thereof, information about the display operation performed when a medical image screen is displayed is set based on the first feature data (subject feature data) of the medical image and the operation information including a predetermined operation and the second feature data (reference feature data) associated with the predetermined operation. Therefore, it is possible to display the medical image using an appropriate process, without using the experience and know-how of the user or the individual image extraction algorithm.

The above-described First to Third Embodiments and of the invention and the modifications thereof are just illustrative, but the invention is not limited to the embodiments. Various modifications of the invention can be made according to, for example, the specifications and it will be apparent from the above description that various other embodiments can be made without departing from the scope and spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image management apparatus, comprising:
an acquiring unit configured to acquire image data corresponding to a series of medical images;
an image processing unit configured to calculate feature data of each medical image included in the series of medical images;
a storage unit configured to store operation information related to a predetermined operation to be performed with respect to a screen on which a medical image is displayed and reference feature data defining a nature of the feature data of the medical image subjected to the predetermined operation;
an operation unit configured to receive input of an operation signal corresponding to operations by a user;
a display operation information setting unit configured to compare the feature data calculated by the image processing unit with the reference feature data stored in the storage unit, and, when the reference feature data having a correspondence to the feature data exist, to set, as information related to a display operation executed when the series of medical images are displayed on a screen, the information related to the predetermined operation associated with the reference feature data having the correspondence;
a control unit configured to execute the display operation in accordance with the information related to the predetermined operation set by the display operation information setting unit when image data included in the series of medical images are played back; and
an operation information generating unit configured to, by associating the reference feature data of the medical image subjected to the predetermined operation, with a content of the operation received by the operation unit and a parameter related to the operation, generate new operation information, when input of the predetermined operation is received by the operation unit.

2. The image management apparatus according to claim 1, wherein the display operation information setting unit sets a parameter used in execution of a predetermined display operation, based on an operation associated with the reference feature data corresponding to the feature data.

3. The image management apparatus according to claim 2, wherein
the predetermined display operation includes an operation of displaying the medical image as a pseudo-moving image, and
the parameter includes a set parameter of a display frame rate in the displaying as the pseudo-moving image.

4. The image management apparatus according to claim 3, wherein the display operation information setting unit changes the set parameter depending on a content of the predetermined operation.

5. The image management apparatus according to claim 4, wherein the predetermined operation includes:

(1) an operation of reducing a playback speed of the medical image;
(2) an operation of repeatedly displaying the medical image;
(3) an operation of temporarily stopping playback of the medical image;
(4) an operation of reversely playing back the medical image;
(5) an operation of enlarging the medical image;
(6) an operation of capturing the medical image;
(7) an operation of adding a comment or a label to the medical image; and
(8) an operation of attaching the captured medical image to a report, and
the display operation information setting unit sets the set parameter according to a priority order that has been set beforehand with respect to operations including the operations (1) to (8) such that the higher a priority is, the lower a display frame rate becomes.

6. The image management apparatus according to claim 4, wherein, when the predetermined operation is an operation of adding a flag to the medical image as being an image of interest or an operation of adding a flag to the medical image as being an image of non-interest, the display operation information setting unit gives a weight to the set parameter according to a flag.

7. The image management apparatus according to claim 2, wherein
the predetermined display operation includes an operation of displaying a medical image extracted from the series of medical images based on a predetermined condition, and
the parameter includes a threshold value used in image extraction.

8. The image management apparatus according to claim 1, wherein the display operation information setting unit is capable of updating the information related to the display operation.

9. The image management apparatus according to claim 1, further comprising a controller configured to generate a screen including the medical image based on the information related to the display operation set by the display operation information setting unit.

10. The image management apparatus according to claim 1, further comprising:
an output unit configured to output the information related to the display operation set by the display operation information setting unit to an external recording device; and
a reading unit configured to read the information related to the display operation from the external recording device.

11. An image management apparatus, comprising:
an operation information storage unit that stores operation information including information related to a predetermined operation performed with respect to a screen on which a medical image is displayed and reference feature data that are feature data of the medical image subjected to the predetermined operation;
an acquiring unit that acquires image data corresponding to a series of medical images;
an image processing unit that calculates feature data of each medical image included in the series of medical images;
a display operation information setting unit that compares the feature data calculated by the image processing unit with the reference feature data stored in the operation information storage unit, and, when the reference feature data having a correspondence to the feature data exist, sets, as information related to a display operation executed when the series of medical images are displayed on a screen, the information related to the predetermined operation associated with the reference feature data having the correspondence;

a first control unit that executes the display operation set by the display operation information setting unit when image data included in the series of medical images are played back;

an operation unit that receives input of an operation to the image management apparatus;

a second control unit that generates a screen including the medical image; and an operation information generating unit that, by associating the reference feature data of the medical image subjected to the predetermined operation, with a content of the operation received by the operation unit and a parameter related to the operation, generates new operation information, when input of the predetermined operation is received by the operation unit.

12. The image management apparatus according to claim 11, wherein the operation information generating unit associates the new operation information with information related to a user who has performed the predetermined operation.

13. The image management apparatus according to claim 11, wherein the operation information generating unit, by calculating an average value or a weighted average value of corresponding feature data in the new operation information and other operation information different from the new operation information, further generates yet other operation information.

14. The image management apparatus according to claim 1, wherein the predetermined operation includes:
an operation of changing a display speed of the medical image;
an operation of repeatedly displaying the medical image;
an operation of temporarily stopping playback of the medical image;
an operation of changing a playback direction of the medical image;
an operation of enlarging or reducing the medical image;
an operation of changing a parameter for display of a medical image;
an operation of capturing the medical image;
an operation of adding a landmark to the medical image;
an operation of adding a comment to the medical image;
an operation of attaching the medical image captured to a report; or
an operation of setting a threshold value for image extraction.

15. The image management apparatus according to claim 11, wherein the predetermined operation includes:
an operation of adding a flag as being an image of interest to the medical image; or
an operation of adding a flag as being an image of non-interest to the medical image.

16. The image management apparatus according to claim 1, wherein the reference feature data and the feature data are at least one of:
an average color of the medical image;
a variation in the average color;
an average brightness of the medical image;
a variation in the average brightness;
a color or brightness of one or a plurality of portions in the medical image;
a variation in the color or brightness of the one or plurality of portions;
a concordance rate between a shape of the one or plurality of portions and a specific pattern;
a similarity or magnitude of a motion vector between the medical image and a medical image adjacent to the medical image;
a parameter indicating a portion included in the medical image; and
a parameter indicating a specific pattern of a spatial frequency obtained by frequency analysis with respect to the medical image.

17. An image management method, comprising:
acquiring image data corresponding to a series of medical images;
calculating feature data of each medical image included in the series of medical images;
providing a storage unit configured to store operation information related to a predetermined operation to be performed with respect to a screen on which a medical image is displayed and reference feature data defining a nature of the feature data of the medical image subjected to the predetermined operation;
receiving input of an operation signal corresponding to operations by a user;
comparing the feature data calculated by the calculating with the reference feature data stored in the storage unit, and, when the reference feature data having a correspondence to the feature data exist, setting, as information related to a display operation executed when the series of medical images are displayed on a screen, the information related to the predetermined operation associated with the reference feature data having the correspondence;
executing the display operation in accordance with the information related to the predetermined operation set by the setting when the image data included in the series of medical images are played back; and
generating, by associating the reference feature data of the medical image subjected to the predetermined operation, with a content of the operation received by the receiving and a parameter related to the operation, new operation information, when input of the predetermined operation is received by the receiving.

18. A non-transitory computer readable storage medium storing an executable program that instructs a processor configured to communicate with a storage unit to execute:
acquiring image data corresponding to a series of medical images;
calculating feature data of each medical image included in the series of medical images;
storing operation information in the storage unit, the operation information including information related to a predetermined operation to be performed with respect to a screen on which a medical image is displayed and reference feature data defining a nature of the feature data of the medical image subjected to the predetermined operation;
receiving input of an operation signal corresponding to operations by a user;
comparing the feature data calculated by the calculating with the reference feature data stored in the storage unit, and, when the reference feature data having a correspondence to the feature data exist, setting, as information related to a display operation executed when the series of medical images are displayed on a screen, the information related to the predetermined operation associated with the reference feature data having the correspondence;

executing the display operation in accordance with the information related to the predetermined operation set by the setting when image data included in the series of medical images are played back; and generating, by associating the reference feature data of the medical image subjected to the predetermined operation, with a content of the operation received by the receiving and a parameter related to the operation, new operation information, when input of the predetermined operation is received by the receiving.

* * * * *